United States Patent [19]

Redikultsev et al.

[11] 4,288,404
[45] Sep. 8, 1981

[54] APPARATUS FOR AUTOMATICALLY STABILIZING A PROCESS OF THERMAL TREATMENT OF LIQUID MEDIA

[76] Inventors: Jury V. Redikultsev, mikroraion "G", 19, kv. 113; Oleg P. Gorbunov, mikroraion "V", 28, kv. 18; Alexandr M. Lomakin, mikroraion "G", 25, kv. 110, all of Puschino Moskovskoi oblasti, U.S.S.R.

[21] Appl. No.: 105,767

[22] Filed: Dec. 20, 1979

[30] Foreign Application Priority Data

Dec. 25, 1978 [SU] U.S.S.R. .............................. 2695900

[51] Int. Cl.³ .......................... A61L 2/04; A61L 2/24
[52] U.S. Cl. ................................... 422/107; 422/109; 422/112; 422/292; 422/295
[58] Field of Search .................. 422/26, 38, 107, 109, 422/112, 295–299, 292; 137/340; 251/61.2

[56] References Cited

U.S. PATENT DOCUMENTS

| | | | |
|---|---|---|---|
| 1,991,026 | 2/1935 | Murray | 422/299 |
| 2,472,970 | 6/1949 | Hanna | 422/26 |
| 4,203,947 | 5/1980 | Young et al. | 422/295 |

*Primary Examiner*—Bradley Garris
*Attorney, Agent, or Firm*—Steinberg & Raskin

[57] ABSTRACT

An apparatus for automatically stabilizing a process of thermal treatment of liquid media comprises a sterilization chamber which is in contact with a heat-exchange jacket, and a device for thermally controlling the process being conducted. The device for thermally controlling the process comprises a coolant flow regulator which is divided by flexible members into three sections. The middle section comprises an overflow valve which is connected by pipelines to a source of a coolant and to the heat exchange jacket, respectively. The two other sections comprise a pressure setting device and a pressure sensor which is connected to the sterilization chamber by means of a pipeline. The pressure setting device and the pressure sensor cooperate with the overflow valve through individual flexible members.

3 Claims, 1 Drawing Figure

U.S. Patent    Sep. 8, 1981    4,288,404
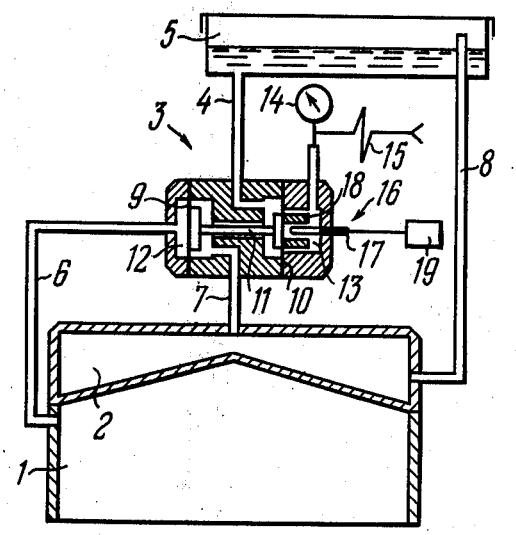

APPARATUS FOR AUTOMATICALLY STABILIZING A PROCESS OF THERMAL TREATMENT OF LIQUID MEDIA

FIELD OF THE ART

The invention relates to production process automatic control systems, and more particularly, to apparatus for automatically stabilizing a process of thermal treatment of liquid media.

The invention may be advantageously used in the medical, microbiological and food industries, as well as in scientific research works.

BACKGROUND OF THE INVENTION

Any production process is characterized by certain physical, chemical and biological parameters. During the process certain ones of the more important parameters should be maintained at a pre-set or corrected level. For that purpose, various automatic control systems are used which consist of three main parts: a meter, a regulator and an actuator. Stepless or relay-type actuators may be used.

Known in the art are apparatus for automatically stabilizing a process of thermal treatment of liquid media, comprising a sterilization chamber which is in contact with a heat-exchange jacket, a device for thermally controlling the process being conducted which is connected to a source of a coolant and communicates with the sterilization chamber and the heat-exchange jacket, such apparatus being described in U.S. Pat. No. 3,445,341 and publicity leaflet by New Brunswick Scientific Co. Inc., model FM-250, Technical Description and Operation Manual.

In such apparatus the device for thermally controlling the process being conducted comprises a temperature sensor which is installed in the sterilization chamber and a valve which is electrically coupled to the temperature sensor, installed in a pipeline connecting the source of a coolant to the heat-exhange jacket. Such apparatus ensures the feeding of a coolant to the sterilization chamber in response to a signal from the sensor.

The above-described apparatus operates in response to a signal from the temperature sensor installed in the sterilization chamber so that the process temperature over the whole volume being sterilized cannot be traced, and only a local zone in which the sensor is installed can be monitored. This monitoring of the sterilization temperature frequently results in incomplete sterilization or overheating of a studied sample. Thermolabile components of solutions, such as glucose, which are sterilized at relatively low temperature and caramelized at increased temperature are especially sensitive to the temperature conditions. In addition, such apparatus have a relay actuation of the valve controlling heat carrier or coolant flow so that as temperature fluctuations in the sterilization chamber occur, the exposure time of a sample changes, and the sample may be deteriorated.

SUMMARY OF THE INVENTION

It is an object of the invention to eliminate temperature fluctuations in the sterilization chamber.

This is accomplished by an apparatus for automatically stabilizing a process of thermal treatment of liquid media, comprising a sterilization or vapor condensation chamber which is in contact with a heat-exchange jacket and a device for thermally controlling the process being conducted which acts as a pressure stabilization unit and which is connected by means of a pipeline to a source of a coolant and communicates with the sterilization chamber and the heat-exchange jacket, wherein according to the invention, the device for thermally controlling the process being conducted comprises a coolant flow regulator which is divided by flexible members into three sections of which the middle section comprises an overflow valve which is connected by means of pipelines to the source of a coolant and to the heat-exchange jacket, respectively, and the two other sections comprise a pressure setting device cooperating with the overflow valve by means of one of the flexible members and a pressure sensor connected by means of a pipeline to the sterilization chamber and cooperating with the overflow valve by means of the other flexible member, respectively.

The pressure setting device is preferably provided with a device for a time tracing of the process performance.

The device for providing a time tracing of the process performance is a circuit which may comprise a hermetically sealed contact built in the pressure setting device, a magnet installed in the pressure setting device on the flexible member and cooperating with the hermetically sealed contact and a time relay electrically coupled to the hermetically sealed contact.

This construction of the apparatus for automatically stabilizing a process of thermal treatment of liquid media according to the invention enables a stepless control of the cross-sectional area of the overflow valve depending on pressure changes in the sterilization chamber thereby steplessly varying the flow through the coolant valve and stabilizing the temperature conditions of sterilization at a pre-set level.

BRIEF DESCRIPTION OF THE DRAWINGS

This and other objects of the invention will become apparent from the following description of specific embodiments of the invention with reference to the accompanying drawing, in which is shown an apparatus according to the invention in longitudinal section.

DETAILED DESCRIPTION OF THE INVENTION

An apparatus for automatically stabilizing a process of thermal treatment of liquid media according to the invention comprises a sterilization or vapor condensation chamber 1 which is in contact with a heat-exchange jacket 2 and a device 3 for thermally controlling the process being conducted which acts as a pressure stabilizing unit and which is connected by means of a pipeline 4 to a source 5 of a coolant, by means of a pipeline 6 to the sterilization chamber 1 and by means of pipelines 7,8 to the heat-exchange jacket 2.

The device 3 for thermally controlling the process being conducted comprises a coolant flow regulator which is divided by means of flexible members, for example membranes 9 and 10 in the illustrated embodiment, into three sections. The middle section which is between the membranes 9 and 10 comprises an overflow valve 11 which is connected by means of the pipelines 4 and 7 to the source 5 of the coolant and to the heat-exchange jacket 2, respectively. The section which is arranged opposite to the membrane 9 comprises a pressure sensor 12 which is connected by means of the pipeline 6 to the sterilization chamber 1 and cooperates with the overflow valve 11 by means of the membrane 9. The section which is arranged opposite to the membrane 10 comprises a pressure setting device 13 which is connected to a pressure gauge 14 coupled to a pressure reducer 15 and to a compressed air source (not shown), the pressure setting device cooperating with the overflow valve 11 through the membrane 10.

The pressure setting device 13 is provided with a device 16 for providing a time tracing of the process performance comprising a circuit including a hermetically sealed contact 17 built in the pressure setting device 13, a magnet 18 installed in the pressure setting device 13 on the membrane 10 and cooperating with the hermetically sealed contact 17 and a time relay 19 electrically coupled to the hermetically sealed contact 17.

In this embodiment the source 5 of a coolant comprises an independent tank containing a coolant which is arranged above the heat-exchange jacket 2.

The apparatus for automatically stabilizing a process of thermal treatment of liquid media according to the invention functions in the following manner.

Operation of the apparatus according to the invention is based on the flow of a coolant through the heat-exchange jacket 2 which depends on steam pressure inside the sterilization chamber.

Air pressure equal to the steam pressure for preselected sterilization conditions is set-up in accordance with the pressure gauge 14 by means of the pressure reducer 15 of the pressure setting device 13. The valve 11 is thus closed upon cooperation with the membrane 10.

Upon heating of the sterilizaton chamber 1 steam pressure in the sensor 12 grows to a value set-up at the pressure setting device 13, whereafter the valve 11 is gradually opened owing to cooperation with the membrane 9, and a coolant from the source 5 is admitted along the pipeline 4 through the valve 11 and along the pipeline 7 to the heat-exchange jacket 2 to lower the temperature in the chamber 1 to the temperature of the preselected sterilization conditions and to maintain it owing to evaporation. The coolant evaporates after passing through the jacket 2 and flows in the form of vapour back to the source 5 of a coolant along the pipeline 8.

An operator determines the time during which the stabilization process cycle is to be maintained so that upon an equalization of the pressure in the pressure setting device 13 and pressure sensor 12, the hermetically sealed contact 17 closes to switch on the time relay 19 which performs the time cycle determined by the operator.

Apparatus for stabilizing a process of thermal treatment of liquid media according to the invention ensures the setting and stabilization of preselected conditions of a liquid medium with insignificant fluctuations of the process parameters, continuous operation of the heat-exchange jacket without its disassembly and cleaning, and sterilization of thermolabile components of solutions.

Specific narrow terminology was used in the description of the embodiment of the invention for the sake of clarity. The invention is not, however, limited by the adopted terms, and it should be born in mind that each such term covers all equivalents functioning identically and used for the same purpose.

While the invention has been described as applied to the preferred embodiment thereof, it is to be understood that changes and modifications may be made by those skilled in the art without departure from the concept and scope of the invention, and such changes and modifications are considered as not deviating from the spirit and scope of the appended claims.

What is claimed is:

1. An apparatus for automatically stabilizing a process of thermal treatment of liquid media, comprising:
   a sterilization chamber;
   a heat-exchange jacket which is in contact with said sterilization chamber;
   a device for thermally controlling the process being conducted which is connected by means of individual pipelines to said sterilization chamber and to said heat-exchange jacket, said device comprising a coolant flow regulator which is divided by first and second flexible members into first, second and third sections, the first section comprising a pressure setting device in which an air pressure equal to the pressure of preselected conditions of the process being conducted is set-up, the second section comprising an overflow valve which is connected by means of said individual pipeline to said heat-exchange jacket and which cooperates with said pressure setting device through said first flexible member, and said third section comprising a pressure sensor which is connected by means of said individual pipeline to said sterilization chamber and cooperates with said overflow valve through the second flexible member; and
   a source of a coolant which is connected by means of an individual pipeline to said overflow valve, the coolant from the source being admitted to said heat-exchange jacket through said overflow valve.

2. An apparatus according to claim 1, wherein said pressure setting device is provided with a device for a time tracing of the process performance.

3. An apparatus according to claim 2, wherein said device for a time tracing of the process performance comprises:
   a hermetically sealed contact built in said pressure setting device;
   a magnet installed in said pressure setting device on the first flexible member and cooperating with said hermetically sealed contact; and
   a time relay electrically coupled to said hermetically sealed contact.

* * * * *